United States Patent [19]

Tari et al.

[11] Patent Number: 4,775,381
[45] Date of Patent: Oct. 4, 1988

[54] HIP PROSTHESIS

[75] Inventors: Gábor Tari, Csongrád; Zoltán Badó, Szentes; Lajos Mészáros; Imre Juhász, both of Hódmezövásárhely, all of Hungary

[73] Assignee: Metripond Merleggyar, Hungary

[21] Appl. No.: 4,243

[22] Filed: Jan. 5, 1987

Related U.S. Application Data

[63] Continuation of Ser. No. 731,052, May 6, 1985, abandoned.

[51] Int. Cl.⁴ .............................................. A61F 2/32
[52] U.S. Cl. .................................. 623/23; 128/92 YZ
[58] Field of Search .................................. 623/16–23; 128/92 YZ

[56] References Cited

U.S. PATENT DOCUMENTS 4,530,115  7/1985  Muller et al. ..................... 128/92 C

FOREIGN PATENT DOCUMENTS 741970  10/1943  Fed. Rep. of Germany ... 128/92 BC

Primary Examiner—Richard J. Apley
Assistant Examiner—David J. Isabella
Attorney, Agent, or Firm—Handal & Morofsky

[57] ABSTRACT

The hip prosthesis according to the invention is a further development of the prosthesis formed with conventional head provided with spherical surface, neck and stem, where a guide profile is formed along the outer straight side of the stem, containing components parallel with the side. The guide profile fits the inner surface of the medullary cavity nail, which allows the simultaneous use of the hip prosthesis and the medullary cavity nail, and nailing of the already prosthetized, then fractured femur.

1 Claim, 3 Drawing Sheets

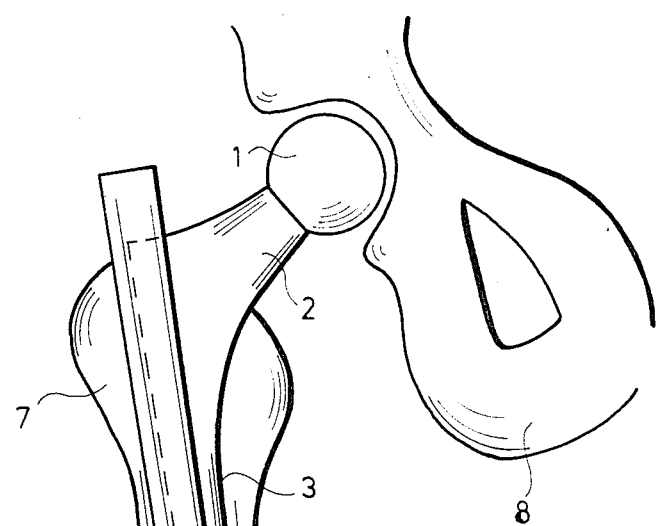
Fig. 5
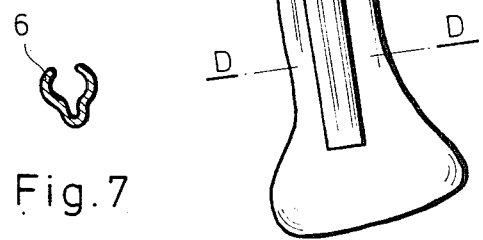
Fig. 6
Fig. 7

HIP PROSTHESIS

This application is a continuation of application Ser. No. 731,052, filed May 6, 1985, abandoned.

FIELD AND BACKGROUND OF THE INVENTION

The present invention relates to a hip prosthesis provided with spherical head, neck and stem with straight side, which allows the nailing of the medullary cavity of the already prosthetized, then fractured femur.

The number of those living with hip prosthesis is increasing more and more at the present time. The number of implanted artificial hip joints is estimated to be two thousand per day. The further increase of the cases into the millions is accounted for by the fact that the diseases of the hip joints due to wear are increasing numerically along with the rapid rise of the age of the population accompanied by a corresponding development of the medical technique.

Recently, however, some disadvantageous properties of hip prosthesis came to light, which initially were not noticeable. It was found that the hip prosthesis is prone to cause fracturing of the femur. This is proven by the increasing number of fractures occurring after prosthesis implantation, and the theoretical explanation of this phenomenon is as follows: the metals implanted into the organism and adapted to the bone do not have the identical elasticity as that of bone. Be it either a plate used for healing of a bone fracture, screwed to any tubular bone, or a metal cemented into the medulla, eventually a fatigue phenomena appears along the boundary of the two types of elastic material, which leads to fracturing of the bone.

The regenerating, defensive mechanism of the living bone working to prevent a fatigue fracture is inhibited particularly in this case—by the fact, that the blood supply of the bone is reduced: about 30% of the blood supply proceeds from the periosteum, and 70% from the medulla. The medulla /replaced by the prosthesis/ is removed, while the bone-glue used for cementing the prosthesis results in further bone damage through the exothermal evolution of heat during the polymeric bond of the bone-glue.

Prosthesis are frequently replaced as a result of dislocation, wear or for other reasons. Replacements are made possible in many cases only by one technique, the surgeon prepares a "knock-out window" at the end of the prosthesis in the bone—the vicinity most prone to fatigue—which extends through one quarter of the circumference of the tubular bone. Thereby breaking down its statics, and damaging the periosteum, which now alone supports the bone. This is proceeded by mechanical and thermal damages. The bone window is refastened generally with additional metals which produce anodic-cathodic effects in the living organism, due to their different metallurgical compositions. This so-called metallosis further damages the already worn out upper third part of the femur, where the stem of the prosthesis ends.

If this part of the non-prosthetized, healthy femur fractures—e.g. in case of accident—the following surgical interventions are possible:

Nailing of the medullary cavity with Küntscher nails. These are shorter or longer shaped steel tubes split along the surface, the lower end of which is provided with edge. These, hammered into the medullarly cavity along the fractured parts, provide stable anchorage, whereby the injured person regains his mobility quickly. Accordingly, this method is used most frequently.

Another method is anchorage with plate and screws, but its stability never reaches that of the nailing of the medullary cavity. At the same time it requires major surgical exposure, repeated operation /removal/, and it causes muscle damage and considerable stress. Breakage of the plate, and repeated fracture of the bone frequently occur. For this reason it is used only in exceptional cases.

Further possibility is the external bone anchorage of the damaged femur, but this is executed in exceptional cases as an emergency method in case of certain open, complicated bone injuries.

The conventional plastering is also known, this however rarely ensures adequate positional bone healing. It is particularly unfavourable in fractures of the femur, because the time of healing is delayed, thereby multiplying the known shortcomings of these treatments generally in case of elderly patients.

SUMMARY OF THE INVENTION

Therefore, the object of the present invention is to provide a hip prosthesis which eliminates the mentioned shortcomings and prevents fracture of the femur and allows the nailing of the medullary cavity of the already prosthetized, then fractured femur.

These and other objects of the invention were achieved by a hip prosthesis wherein a guide profile is formed on the stem, along the outer straight side thereof, the generatrices of which are parallel with this side. The guide profile suitably fits the inner surface of the conventional nails of the medullary cavity which allows the sliding of the medullary cavity nail on the guide profile of the hip prosthesis similarly like on a rail.

The present invention enables the implantation of the hip prosthesis and to be joined to the medullary cavity nail by the above-noted sliding metallic contact.

Further fundamental benefit of the invention is that implantation of the stem does not necessarily require anchorage with bone-glue, since the bearing along a long surface and the tapered form of the stem result in gomphosis, which is an adequate anchorage in most cases.

The invention provides still further benefits following the implantation of the hip prosthesis. Namely, the most frequent complication of the hip prosthesis is the dislocation. This is helped by replacement of the prosthesis. However, this complication does not arise in case of the hip prosthesis according to the invention, since the medullary cavity nail moving on its guide-rail wedges itself repeatedly, performing a self-healing, spontaneous correction without endangering the knee joint when the medullary cavity nail is moving off its position.

The nail of the medullary cavity can be removed separately, or the stem replaced without removal of the nail after the fracture of the femur is healed.

BRIEF DESCRIPTION OF THE DRAWINGS

Further details of the invention are described by way of example, with the aid of drawing, in which:

FIG. 5 is a combined application of the hip prosthesis and a nail of the medullary cavity, FIG. 6 is a section along C—C of FIG. 5, FIG. 7 is a section along D—D of FIG. 5.

DESCRIPTION OF PREFERRED EMBODIMENT

FIGS. 1 to 4 show an embodiment of the hip prosthesis according to the invention consisting of the customary parts. Head 1 provided with spherical surface fits the neck 2. The neck 2 is at obtuse angle to the stem 3 and the outer side 4 of the stem 3 is straight contrary to the generally used hip prostheses. Such stems were used earlier for elongated stem and tumor prostheses.

The stem 3 and neck 2 are jointed without the customary collar. This is a suitable formation in this cause, because the neck part does not inhibit the repeated gomphosis of the prosthesis or its inevitable displacement upon wear.

Figure 1:
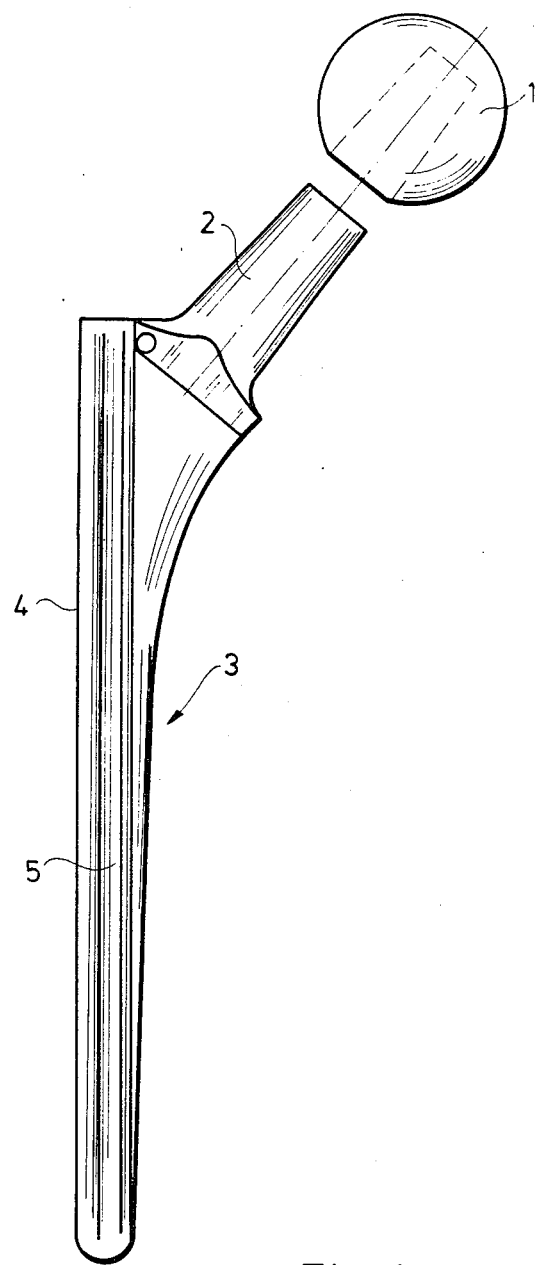
FIG. 1 is a side view of the hip prosthesis according to the invention.
Figure 3:
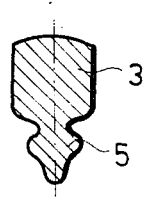
FIG. 3 is a section along A—A.
Figure 4:
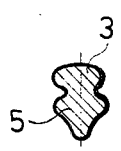
FIG. 4 is a section along B—B.
Figure 2:
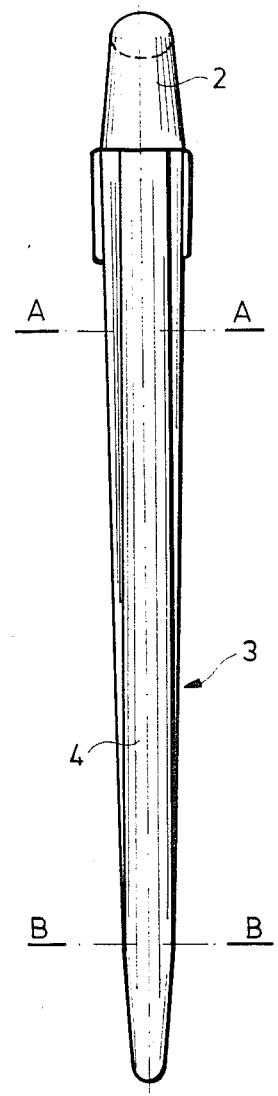
FIG. 2 is a front view of the hip prosthesis shown in FIG. 1.

The cross section of stem 3 narrows down as shown in FIGS. 2, 3, 4. However, the outer side 4 of the stem 3 is provided with guide profile 5 contrary to the usual one. Its cross section along stem 3 is constant, that is, it does not decrease as the cross section of stem 3. The surface of the guide profile 5 consists of profile generatrices running parallel with the side 4 and thus it forms a suitable guiding surface parallel with the stem 3.

The guide profile 5 is formed to mate the inner surface of the conventional medullary cavity nails and thus it serves as their guide.

FIGS. 5, 6 and 7 show the connection of the hip prosthesis, according to the invention, to the conventional medullary cavity nail 6 and its application in case of fracture of the bone.

As seen, the treatment of the bone fracture takes place by hammering the medullary cavity nail 6 into the femur 7, followed by the simple and safe implantation of the hip prosthesis according to the invention. This is carried out in a simple way by fitting the guide profile 5 on the side 4 of stem 3 into the medullary cavity nail 6 and moving it as on a rail, it is hammered into position as shown in FIG. 6. Upon fitting part 2 of the hip prosthesis into the coxal 8, the implantation is completed.

The lower end of the medullary cavity nail 6 as shown in FIG. 7 contacts the end of the femur 7 at the knee joint and thus its dislocation is practically excluded.

As mentioned earlier, the incidental disengagement of the hip prosthesis is automatically corrected by sliding in the medullary cavity nail.

In view of the foregoing, the hip prosthesis according to the invention solves the problem connected with the treatment of the worn out hip joint by hip prosthesis, namely the healing of the frequent fractures of the femur. This increases not only the safety of the operations and facilitates the work of the surgeons, but it reduces the incidental aversion of the patients related to the hip prosthesis.

What we claim is:

1. A prosthesis for a fracture of an already prosthetized hip comprising, in combination:

a stem having at a first end thereof an integrally formed neck portion and a spherical head disposed on the neck portion, the stem having a straight side extending from below the neck portion to a second end of the stem, and a profiled guide having a constant cross-section formed along a side of the stem opposite to the straight side, the profiled guide extending uninterrupted from the neck portion to the second end, the profiled guide comprising a curvilinear cross-section forming a rail-like portion, and an elongated medullary cavity nail, said nail being tubular and having a longitudinally extending inner surface which has a constant cross-section complimentary to the rail-like portion, the inner surface extending for a length greater than the length of the rail-like portion, whereby the nail inner surface mates in sliding and secure engagement with the profiled guide during insertion of the nail in the medullary cavity such that the nail extends beyond the second end of the stem.

* * * * *